United States Patent

Oakley et al.

[11] Patent Number: 5,225,407
[45] Date of Patent: Jul. 6, 1993

[54] 5-HT₃ RECEPTOR ANTAGONISTS FOR THE TREATMENT OF AUTISM

[75] Inventors: Nigel R. Oakley, Cambridge; Ian H. Coates, Hertford; Peter C. North; Alexander W. Oxford, both of Royston, all of England

[73] Assignee: Glaxo Group Limited, London, England

[21] Appl. No.: 941,951

[22] Filed: Sep. 8, 1992

Related U.S. Application Data

[63] Continuation of Ser. No. 07/658,685, Feb. 21, 1991, abandoned.

[30] Foreign Application Priority Data

Feb. 22, 1990 [GB] United Kingdom ............... 90 04015
Feb. 22, 1990 [GB] United Kingdom ............... 90 04044

[51] Int. Cl.⁵ ..................... A61K 31/55; A61K 31/44
[52] U.S. Cl. ..................................... 514/215; 514/292
[58] Field of Search ..................... 514/397, 215, 292

[56] References Cited

U.S. PATENT DOCUMENTS

| | | | |
|---|---|---|---|
| 4,695,578 | 9/1987 | Coates et al. | 514/397 |
| 4,985,422 | 1/1991 | North et al. | 514/215 |
| 5,008,272 | 4/1991 | Coates et al. | 514/292 |

FOREIGN PATENT DOCUMENTS

| | | |
|---|---|---|
| 0229444 | 7/1987 | European Pat. Off. |
| 0275668 | 7/1988 | European Pat. Off. |
| 0276559 | 8/1988 | European Pat. Off. |
| 0278161 | 8/1988 | European Pat. Off. |
| 0411900A2 | 2/1991 | European Pat. Off. |
| 2193633A | 2/1988 | United Kingdom |
| WO90/12569 | 11/1990 | World Int. Prop. O. |

OTHER PUBLICATIONS

The Merck Manual, 14th edition (1982), MSD Publisher, pp. 1900–1902.

Primary Examiner—Frederick E. Waddell
Assistant Examiner—Raymond J. Henley, III
Attorney, Agent, or Firm—Bacon & Thomas

[57] ABSTRACT

The invention relates to the use of a compound which acts as an antagonist of 5-HT at 5-HT₃ receptors in the treatment of autism or another disorder originating in childhood in which there is mental retardation.

11 Claims, No Drawings

5-HT₃ RECEPTOR ANTAGONISTS FOR THE TREATMENT OF AUTISM

This application is a continuation of application Ser. No. 07/658,685, filed Feb. 21, 1991, now abandoned.

This invention relates to a new medical use for certain chemical compounds and pharmaceutical compositions containing them. In particular it relates to the use in the treatment of mental disorders originating in childhood of compounds which act as antagonists of 5-hydroxytryptamine (5-HT) at 5-HT$_3$ receptors. Such receptors have been described for example by Fozard et al., Eur. J. Pharmacol., 1979, 59, 195–210; Ireland, Straughan and Tyers, Br. J. Pharmacol., 1982, 75, 16P; Humphrey, Neuropharm., 1984, 23, 1503–1570; Richardson et al., Nature, 1985, 316, 126–131; and Bradley et al., Neuropharm., 1986, 25, 563–576.

5-HT$_3$ receptors of this type are located, for example, on the terminals of afferent sensory neurones, and are also present in the central nervous system. Compounds which act as antagonists of 5-HT at 5-HT$_3$ receptors may be identified using standard tests, for example, in vitro by measuring their inhibition of the depolarising effect of 5-HT on the rat or rabbit isolated vagus nerve, or the tachycardia produced by 5-HT in the rabbit isolated heart or the contraction produced by 5-HT in the guinea-pig isolated ileum, or in vivo by measuring their effect on the Von Bezold-Jarisch reflex (induced by 5-HT) as described, for example, in the above-mentioned references.

A variety of compounds which act as antagonists of 5-HT at 5-HT$_3$ receptors have been described in the art. These compounds are generally azabicyclo derivatives and/or benzoic acid derivatives, or imidazole derivatives. The azabicyclo derivatives include compounds containing a bridged piperidyl group, such as a tropyl, pseudotropyl, homotropyl or quinuclidinyl group, and they preferably contain a carbocyclic or heterocyclic aromatic group linked, for example as an ester or amide, to the azabicyclic ring. The aromatic group may be for example an optionally substituted phenyl, indolyl, benzofuranyl, benzothienyl, benzisoxazolyl, indazolyl or pyrimidinyl group.

The benzoic acid derivatives which act as antagonists of 5-HT at 5-HT$_3$ receptors include benzoates and benzamides, for example esters or amides formed with an azabicyclic group as defined above, or formed with a piperidyl group.

5-HT$_3$ receptor antagonists have been found to be anti-emetics, being particularly effective against chemotherapy and radiotherapy induced emesis, and against post-operative nausea and vomiting.

Compounds having 5-HT$_3$ receptor antagonist activity have also been described as being useful in the treatment of psychotic disorders such as schizophrenia, anxiety, depression, mania, obesity, bulimia (and other conditions associated with excessive eating), cognitive disorders such as Alzheimer's disease, and dependency on drugs and substances of abuse.

5-HT$_3$ receptor antagonists have also been shown to promote gastric emptying, and are thus useful in the treatment of conditions which may be relieved by the promotion of gastric emptying. Such conditions include gastric stasis and symptoms of gastrointestinal dysfunction such as dyspepsia, reflux oesophagitis, peptic ulcer and flatulence. Other conditions in which 5-HT$_3$ antagonists may be effective include irritable bowel syndrome, and pain, particularly the pain associated with migraine.

It has now been found that compounds which act as antagonists of 5-HT at 5-HT$_3$ receptors may be useful for the treatment of mental disorders which are first manifest in childhood, more particularly autism. This is a severely debilitating condition, characterised by a range of symptoms including mental retardation, self isolation, stereotyped behaviour, language disability, cognitive deficits, sensory-motor integration imbalance, and disturbances of sleep pattern. Such symptoms are usually evident within the first two or three years of life, and frequently persist into adulthood. 5-HT$_3$ antagonists may also be useful for the treatment of other disorders originating in childhood in which there is mental retardation, such as phenylketonuria (PKU) and Down's syndrome.

Accordingly the invention provides a method of treatment of a human subject suffering from autism or another disorder originating in childhood in which there is mental retardation, which comprises administering to the subject an effective amount of a compound which acts as an antagonist of 5-HT at 5-HT$_3$ receptors.

References in this specification to treatment include prophylactic treatment as well as the acute alleviation of symptoms.

Preferred compounds for use according to the invention are those compounds which act as antagonists of 5-HT at 5-HT$_3$ receptors described in published UK patent application Nos. 2100259, 2125398, 2153821, 2160871 and 2202530; published European patent applications Nos. 94724, 99789, 200444, 242973, 247266, 266730, 302699, 306323, 307172, 309423, 313393, 337547, 339950, 353983, 356098, 358903, 381422, 397364 and 397365; and PCT Patent Application No. 88/01866.

A particularly preferred 5-HT$_3$ antagonist for use according to the invention is:

1,2,3,9-tetrahydro-9-methyl-3-[(2-methyl-1H-imidazol-1-yl)methyl]-4H-carbazol-4-one (also known as ondansetron) and physiologically acceptable salts and solvates thereof. A preferred form of this compound is the hydrochloride dihydrate.

Other preferred 5-HT$_3$ antagonists for use according to the invention include:
indol-3-yl carboxylic acid endo-8-methyl-8-azabicylo[3.2.1]oct-3-yl ester (also known as tropisetron) (ICS 205-930);
endo-N-(9-methyl-9-azabicyclo[3.3.1]non-3-yl)-1-methyl-indazole-3-carboxamide (also known as granisetron) (BRL 43694);
endo-N-(8-methyl-8-azabicyclo[3.2.1]oct-3-yl)-2,3-dihydro-3,3-dimethylindole-1-carboxamide;
4-amino-N-(1-azabicyclo[2.2.2]oct-3-yl)-5-chloro-2-methoxybenzamide (also known as zacopride), in optically active form, preferably the R (+) form, or in racemic form;
indole-3-carboxylic acid octahydro-3-oxo-2,6-methano-2H-quinolizin-8-yl ester (MDL 73147), particularly in the form of its methanesulphonate; and physiologically acceptable salts and solvates thereof.

Yet other preferred 5-HT$_3$ antagonists for use according to the invention include:
4-amino-5-chloro-N-[2-(diethylamino)ethyl]-2-(1-methyl-2-oxopropoxy)benzamide (also known as batanopride) BMY 25081;
1-methyl-N-(8-methyl-8-azabicyclo[3.2.1]oct-3-yl)-1H-indazole-3-carboxamide (LY 278584);

endo-5-chloro-2,3-dihydro-2,2-dimethyl-N-(8-methyl-8-azabicyclo[3.2.1]oct-3-yl)-7-benzofurancarboxamide (LY 277359);

(S)-4-amino-5-chloro-N-(2-pyrrolidinylmethyl)-2,3-dihydrobenzo[b]furan-7-carboxamide (ADR 851);

(S)-5-chloro-N-(2-pyrrolidinylmethyl)-2,3-dihydrobenzo[b]furan-7-carboxamide (ADR847);

4-[N-(1-azabicyclo[2.2.2]octan-3-(S)-yl)]-2-chloro-cis-5a-(S)-9a-(S)-5a,6,7,8,9,9a-hexahydrobenzofurancarboxamide (RG12915);

2'-(1-methyl-1H-indol-3-yl)-spiro(1-azabicyclo[2.2.2]octane)-3,5'-4H-oxazole (L 683877);

N-[1-methyl-4-(3-methylbenzyl)hexahydro-1H-1,4-diazepin-6-yl]-1H-indazole-3-carboxamide (AS 5370);

(±)-N-1-azabicyclo[2.2.2]oct-3-yl)-6-chloro-4-methyl-3-oxo-3,4-dihydro-2H-1,4-benzoxazine-8-carboxamide (Y 25130);

4,5,6,7-tetrahydro-5-[(1-methylindol-3-yl)carbonyl]benzimidazole (YM 060);

(±)-4-amino-N-(1-azabicyclo[2.2.2]oct-3-yl)-5-chloro-2-(cyclopropylmethoxy)benzamide (also known as pancopride) (LAS 30451);

N(endo-8-methyl-8-azabicyclo[3.2.1]oct-3-yl)-2,3-dihydro-2-oxo-1H-benzimidazole-1-carboxamide (DAU 6215);

4-[[(1-azabicyclo[2.2.2]oct-2-en-2-yl)methyl]aminocarbonyl]-2-chloro-5-methoxybenzene-1-amine;

4-(2-methoxyphenyl)-2-[(5-methyl-4-imidazolyl)methyl]thiazole; 3-[2-(guanidinylmethyl)-4-thiazolyl]indole;

(2α-6β-9aα)-4-amino-5-chloro-2-methoxy-N-tropanyl-benzamide (BRL 24682);

(±)-endo-4-amino-5-chloro-2-methoxy-N-(1-azabicylo[3.3.1]non-4-yl)benzamide (also known as renzapride) (BRL 24924), particularly in the form of its hydrochloride hydrate;

4-amino-5-chloro-2-methoxy-N-(1,2-diethyl-4-pyrazolidinyl)benzamide (also known as dazopride);

1αH, 3α, 5αH-tropan-3-yl-3,5-dimethylbenzoate (MDL 72422);

1αH, 3α, 5αH-tropan-3-yl-3,5-dichlorobenzoate (MDL 72222); 3-(5-methyl-1H-imidazol-4-yl)-1-(1-methyl-1H-indol-3-yl)-1-propanone (GR 65630);

2,5-dihydro-5-methyl-2-[(5-methyl-1H-imidazol-4-yl)methyl]-1H-pyrido[4,3-b]indol-1-one;

and physiologically acceptable salts and solvates thereof.

A preferred group of 5-HT₃ antagonists for use according to the invention is that represented by the formula (I):

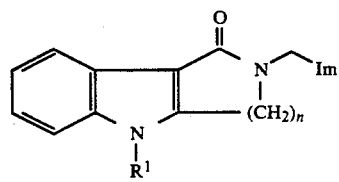

In the above formula Im represents an imidazolyl group of formula:

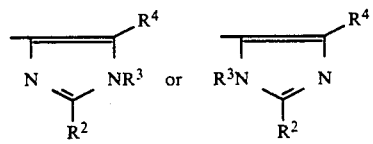

and R¹ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, phenylmethoxymethyl, phenoxyethyl, phenoxymethyl, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl-group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same or different, represents a hydrogen atom or a $C_{1-6}$alkyl group;

and n represents 2 or 3. and their physiologically acceptable salts and solvates.

Preferred compounds of formula (I) for use according to the invention are:

2,3,4,5-tetrahydro-5-(phenylmethyl)-2-[(5-methyl-1H-imidazol-4-yl)methyl]-1H-pyrido[4,3-b]indol-1-one;

5-cyclopentyl-2,3,4,5-tetrahydro-2-[(5-methyl-1H-imidazol-4-yl)methyl]-1H-pyrido[4,3-b]indol-1-one;

2,3,4,5-tetrahydro-2-[(5-methyl-1H-imidazol-4-yl)methyl]-5-propyl-1H-pyrido[4,3-b]indol-1-one;

5-(cyclopentylmethyl)-2,3,4,5-tetrahydro-2-[(5-methyl-1H-imidazol-4-yl)methyl]-1H-pyrido[4,3-b]indol-1-one;

3,4,5,6-tetrahydro-6-methyl-2-[(5-methyl-1H-imidazol-4-yl)methyl]-azepino[4,3-b]indol-1(2H)-one;

2,3,4,5-tetrahydro-N,N-dimethyl-2-[(5-methyl-1H-imidazol-4-yl)-methyl]-1-oxo-5H-pyrido[4,3-b]indole-5-carboxamide;

2,3,4,5-tetrahydro-2-[(5-methyl-1H-imidazol-4-yl)methyl]-5-(2-propynyl)-1H-pyrido[4,3-b]indol-1-one;

5-ethyl-2,3,4,5-tetrahydro-2-[(5-methyl-1H-imidazol-4-yl)methyl]-1H-pyrido[4,3-b]indol-1-one;

2,3,4,5-tetrahydro-5-(1-methylethyl)-2-[(5-methyl-1H-imidazol-4-yl)-methyl]-1H-pyrido[4,3-b]indol-1-one;

2,3,4,5-tetrahydro-2-[(5-methyl-1H-imidazol-4-yl)methyl]-1H-pyrido-[4,3-b]indol-1-one;

and their physiologically acceptable salts and solvates.

A particularly preferred compound of formula (I) for use according to the invention is 2,3,4,5-tetrahydro-5-methyl-2-[(5-methyl-1H-imidazol-4-yl)methyl]-1H-pyrido[4,3-b]indol-1-one and its physiologically acceptable salts and solvates. Preferred salts of this compound are the hydrochloride and maleate, of which the hydrochloride is particularly preferred.

A further preferred group of 5-HT₃ antagonists for use according to the invention is that represented by the formula (II):

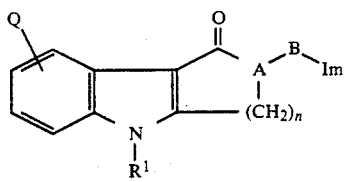 (II)

wherein Im represents an imidazolyl group of the formula:

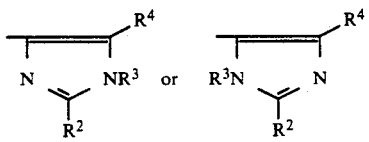

$R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl- group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl-group, and each of the other two groups, which may be the same or different, represents a hydrogen atom or a $C_{1-6}$alkyl group;

Q represents a hydrogen or a halogen atom, or a hydroxy, $C_{1-4}$alkoxy, phenyl$C_{1-3}$alkoxy- or $C_{1-6}$alkyl group or a group —$NR^7R^8$ or —$CONR^7R^8$ wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring);

n represents 1, 2 or 3; and A-B represents the group CH—$CH_2$ or C=CH; and their physiologically acceptable salts and solvates.

A preferred compound of formula (II) for use according to the invention is:

(±)-1,2,3,9-tetrahydro-9-methyl-3-[(5-methyl-1H-imidazol-4-yl)methyl]-4H-carbazol-4-one, and optical isomers thereof, namely:

(±)-1,2,3,9-tetrahydro-9-methyl-3-[(5-methyl-1H-imidazol-4-yl)methyl]-4H-carbazol-4-one, and;

(−)-1,2,3,9-tetrahydro-9-methyl-3-[(5-methyl-1H-imidazol-4-yl)methyl]-4H-carbazol-4-one;

and physiologically acceptable salts and solvates thereof.

A yet further preferred group of 5-HT₃ antagonists for use according to the invention is that represented by the formula (III):

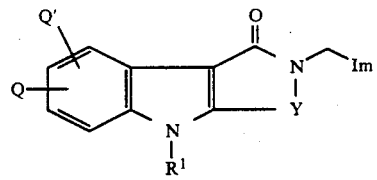 (III)

wherein Im represents an imidazolyl group of the formula:

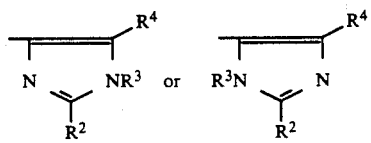

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl-group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same or different, represents a hydrogen atom or a $C_{1-6}$alkyl group;

Y represents the group CH=CH or $(CH_2)_n$, wherein n represents 2 or 3;

Q represents a halogen atom, or a group selected from hydroxy, $C_{1-4}$alkoxy, phenyl$C_{1-3}$alkoxy-, $C_{1-6}$alkyl, cyano, phenyl which may be unsubstituted or substituted by one or more $C_{1-4}$alkyl, $C_{1-4}$alkoxy or hydroxy groups or halogen atoms, —$NR^7R^8$, —$CONR^7R^8$ or —$(CH_2)_pCONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring; and p represents 1,2 or 3), —$(CH_2)_qNR^9R^{10}$ (wherein $R^9$ represents a hydrogen atom or a $C_{1-4}$alkyl group, and $R^{10}$ represents a group —$COR^{11}$ or —$SO_2R^{11}$ wherein $R^{11}$ represents a $C_{1-4}$alkyl group; and q represents 0,1,2 or 3), or —$(CH_2)_2CO_2R^{11}$($R^{11}$ being as defined previously);

Q' represents a hydrogen or a fluorine atom; and physiologically acceptable salts and solvates thereof.

Preferred compounds of formula (III) for use according to the invention are:

6-fluoro-2,3,4,5-tetrahydro-5-methyl-2-[(5-methyl-1H-imidazol-4-yl)-methyl]-1H-pyrido[4,3-b]indol-1-one;

2,3,4,5-tetrahydro-5,6-dimethyl-2-[(5-methyl-1H-imidazol-4-yl)-methyl]-1H-pyrido[4,3-b]indol-1-one;

6,9-difluoro-2,3,4,5-tetrahydro-5-methyl-2-[(5-methyl-1H-imidazol-4-yl)methyl]-1H-pyrido[4,3-b]indol-1-one;

6-fluoro-2,3,4,5-tetrahydro-2-[(5-methyl-1H-imidazol-4-yl)methyl]-5-(2-propynyl)-1H-pyrido[4,3-b]indol-1-one;

2,3,4,5-tetrahydro-5-methyl-2-[(5-methyl-1H-imidazol-4-yl)methyl]-1-oxo-1H-pyrido[4,3-b]indole-6-carbonitrile; and their physiologically acceptable salts and solvates.

In a further aspect, the invention provides a pharmaceutical composition which comprises an effective amount of a compound which acts as an antagonist of 5-HT at 5-HT$_3$ receptors for use in medicine, particularly human medicine, for the treatment of autism or another disorder originating in childhood in which there is mental retardation.

In a yet further aspect, the invention provides for the use of a compound which acts an an antagonist of 5-HT at 5-HT$_3$ receptors, for the manufacture of a medicament for the treatment of autism or another disorder originating in childhood in which there is mental retardation.

Pharmaceutical compositions for use in accordance with the present invention may be formulated in conventional manner using one or more physiologically acceptable carriers or excipients.

Thus the compounds for use according to the present invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for use according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds for use according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds for use according to the may be formulated with suitable polymeric or hydrophobic materials (for example as an emulsion in an acceptable oil) or ion exchange resins, or as sparingly soluble derivatives, for example, as a sparingly soluble salt.

A proposed dose of the compounds for use according to the invention for administration to a human (of approximately 70 kg body weight) is 0.001 to 10 mg, preferably 0.01 to 1 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated.

The following examples illustrate pharmaceutical formulations for use according to the invention, containing 1,2,3,9-tetrahydro-9-methyl-3-[(2-methyl-1H-imidazol-1-yl)methyl]-4H-carbazol-4-one hydrochloride dihydrate as the active ingredient (1.25 g of the hydrochloride dihydrate contains 1.00 g of the free base).

Other compounds which are antagonists of 5-HT at 5-HT$_3$ receptors may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression Tablet | mg/tablet |
| --- | --- |
| (i) Active Ingredient | 4.688 |
| Calcium Hydrogen Phosphate BP* | 83.06 |
| Croscarmellose Sodium NF | 1.8 |
| Magnesium Stearate BP | 0.45 |
| Compression weight | 90.0 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| | mg/tablet |
| --- | --- |
| (ii) Active Ingredient | 0.31 |
| Anhydrous Lactose USNF | 131.99 |
| Pregelatinised Starch USNF | 7.0 |
| Magnesium Stearate BP | 0.7 |

| mg/tablet | |
|---|---|
| Compression weight | 140.0 |

The active ingredient is passed through a 60 mesh sieve, and blended with the lactose, pregelatinised starch and magnesium stearate. The resultant mix is compressed into tablets using a Manesty F3 tablet machine fitted with 7.5 mm normal concave punches.

SYRUP

This may be either a sucrose or sucrose free presentation.

| A. Sucrose Syrup | mg/5 ml dose |
|---|---|
| Active Ingredient | 2.5 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-free Syrup | mg/5 ml dose |
|---|---|
| Active Ingredient | 2.5 |
| Hydroxypropylmethylcellulose USP (viscosity type 4000) | 22.5 |
| Buffer | |
| Flavour | |
| Colour | as require |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

| | $\mu$g/ml |
|---|---|
| (i) Active Ingredient | 800 |
| Dilute Hydrochloric Acid BP to pH 3.5 | |
| Sodium Chloride Injection BP to 1 ml | |

The active ingredient is dissolved in a suitable volume of Sodium Chloride Injection BP, the pH of the resultant solution is adjusted to pH3.5 with dilute hydrochloric acid BP then the solution is made to volume with sodium chloride injection BP and thoroughly mixed. The solution is filled into Type 1 clear glass 5 ml ampoules which are sealed under a headspace of air, by fusion of the glass then sterilised by autoclaving at 120° for not less than 15 minutes.

| | $\mu$g/ml |
|---|---|
| (ii) Active ingredient | 56.2 |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A method for the treatment of autism or another disorder originating in childhood in which there is mental retardation which comprises administering to a human subject an effective amount of a compound which acts as an antagonist of 5-hydroxytryptamine (5-HT) at 5-HT$_3$ receptors.

2. A method according to claim 1 wherein the compound which acts as an antagonist of 5-HT at 5-HT$_3$ receptors is ondansetron or a physiologically acceptable salt or solvate thereof.

3. A method according to claim 2 wherein the ondansetron is in the form of its hydrochloride dihydrate.

4. A method according to claim 1 wherein the compound which acts as an antagonist of 5-HT at 5-HT$_3$ receptors is selected from:
indol-3-yl carboxylic acid endo-8-methyl-8-azabicylo[3.2.1]oct-3-yl ester; endo-N-(9-methyl-9-azabicyclo[3.3.1]non-3-yl)-1-methyl-indazole-3-carboxamide;
endo-N-(8-methyl-8-azabicyclo[3.2.1]oct-3-yl)-2,3-dihydro-3,3-dimethylindole-1-carboxamide;
4-amino-N-(1-azabicyclo[2.2.2]oct-3-yl)-5-chloro-2-methoxybenzamide; indole-3-carboxylic acid octahydro-3-oxo-2,6-methano-2H-quinolizin-8-yl ester; and physiologically acceptable salts and solvates thereof.

5. A method according to claim 1 wherein the compound which acts as an antagonist of 5-HT at 5-HT$_3$ receptors is a compound of formula (I):

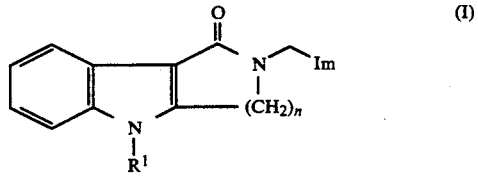

wherein Im represents an imidazolyl group of formula:

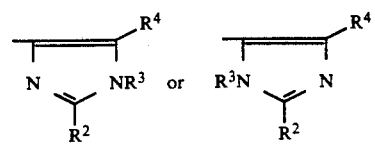

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, phenylmethoxymethyl, phenoxyethyl, phenoxymethyl, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl- group, in which the phenyl group is unsubstituted or substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same or different, represents a hydrogen atom or a $C_{1-6}$alkyl group;

and n represents 2 or 3.

or a physiologically acceptable salt or solvate thereof.

6. A method according to claim 5 wherein the compound of formula (I) is 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

7. A method according to claim 1 wherein said compound is administered in the form of a medicament adapted for oral, buccal, parenteral, rectal or transdermal administration or in a form adapted for administration by inhalation or insufflation.

8. A method according to claim 1 wherein said compound is administered in the form of a medicament in unit dose form containing from 0.001 to 10 mg of active ingredient per unit dose expressed as the weight of free base.

9. A method according to claim 8, wherein the amount of active ingredient per unit dose is from 0.01 to 1 mg.

10. A method according to claim 6 wherein the compound is in the form of its hydrochloride salt.

11. A method according to claim 1 wherein the compound which acts as an antagonist of 5-HT at 5-$HT_3$ receptors is (+)-1,2,3,9-tetrahydro-9-methyl-3-[(5-methyl-1H-imidazol-4-yl)methyl]-4H-carbazol-4-one or a physiologically acceptable salt or solvate thereof.

* * * * *